(12) United States Patent
Cobanoglu et al.

(10) Patent No.: US 10,613,047 B2
(45) Date of Patent: Apr. 7, 2020

(54) FABRIC WITH DEGRADABLE SENSOR

(71) Applicant: Sanko Tekstil Isletmeleri San. Ve Tic. A.S., Inegol-Bursa (TR)

(72) Inventors: Ozgur Cobanoglu, Inegol-Bursa (TR); Jitka Eryilmaz, Inegol-Bursa (TR); Ozgur Akdemir, Inegol-Bursa (TR); Deniz Iyidogan, Inegol-Bursa (TR); Onur Yukselen, Inegol-Bursa (TR)

(73) Assignee: Sanko Tekstil Isletmeleri San. Ve Tic. A.S., Inegol-Bursa (TR)

( * ) Notice: Subject to any disclaimer, the term of this patent is extended or adjusted under 35 U.S.C. 154(b) by 449 days.

(21) Appl. No.: 15/229,579

(22) Filed: Aug. 5, 2016

(65) Prior Publication Data

US 2017/0038322 A1 Feb. 9, 2017

(30) Foreign Application Priority Data

Aug. 7, 2015 (EP) .................................... 15180240

(51) Int. Cl.
| | |
|---|---|
| *G01N 27/02* | (2006.01) |
| *A41D 1/00* | (2018.01) |
| *A41D 1/06* | (2006.01) |
| *G01N 33/36* | (2006.01) |
| *D03D 1/00* | (2006.01) |
| *G01D 5/16* | (2006.01) |
| *G06K 19/07* | (2006.01) |

(52) U.S. Cl.
CPC ............. *G01N 27/02* (2013.01); *A41D 1/002* (2013.01); *A41D 1/06* (2013.01); *D03D 1/0088* (2013.01); *G01D 5/16* (2013.01); *G01N 33/367* (2013.01); *A41D 2500/10* (2013.01); *A41D 2500/20* (2013.01); *D10B 2401/18* (2013.01); *G06K 19/0717* (2013.01)

(58) Field of Classification Search
CPC ........ G01N 27/02; G01N 33/367; G01N 3/56; G01N 33/36; G01N 33/365; A41D 1/06; A41D 1/002; A41D 2500/20; A41D 2500/10; D03D 1/0088; D10B 2401/18; G06K 19/0717
USPC ....................................................... 324/654
See application file for complete search history.

(56) References Cited

U.S. PATENT DOCUMENTS

| | | |
|---|---|---|
| 6,687,523 B1 | 2/2004 | Jayaramen et al. |
| 6,727,197 B1 | 4/2004 | Wilson et al. |
| (Continued) | | |

FOREIGN PATENT DOCUMENTS

WO 2017017260 2/2017

OTHER PUBLICATIONS

International preliminary report on patentability dated Feb. 13, 2018 for PCT/EP2016/068740.

(Continued)

*Primary Examiner* — Patrick Assouad
*Assistant Examiner* — Haidong Zhang
(74) *Attorney, Agent, or Firm* — Silvia Salvadori

(57) ABSTRACT

A fabric comprising at least one conductive element to define at least one portion of an electric circuit, and a sensor coupled to said conductive element, wherein the sensor comprises a degradable element configured to at least partially degrade in preset conditions to change an electric feature of said sensor. An article comprising the fabric and a process for monitoring the life-cycle of the fabric are also disclosed.

25 Claims, 13 Drawing Sheets

(56) References Cited

U.S. PATENT DOCUMENTS

| | | | |
|---|---|---|---|
| 2005/0012616 A1* | 1/2005 | Forster | G06K 19/0717 |
| | | | 340/572.7 |
| 2005/0258717 A1* | 11/2005 | Mullen | A43B 3/00 |
| | | | 310/339 |
| 2010/0123583 A1 | 5/2010 | Bommer et al. | |
| 2013/0020313 A1* | 1/2013 | Swallow | D03D 1/0088 |
| | | | 219/545 |
| 2014/0180624 A1 | 6/2014 | Nikonov et al. | |
| 2016/0245665 A1* | 8/2016 | Logan | G07C 3/00 |
| 2016/0275775 A1* | 9/2016 | Glasgow | G08B 21/182 |

OTHER PUBLICATIONS

International Search Report and Written Opinion from related application PCT/EP2016/068740, dated Oct. 7, 2016.

European Search Report and Written Opinion from priority application EP 15180240.2, dated Nov. 4, 2015.

\* cited by examiner

FABRIC WITH DEGRADABLE SENSOR

RELATED APPLICATION

This application claims priority to European Application No. EP 15180240.2 filed 7 Aug. 2015, the contents of which are hereby incorporated by reference as if set forth in their entirety.

TECHNICAL FIELD

The present invention relates to a fabric and a garment having such a fabric to monitor the life-cycle of the garment, and in particular to monitor the number of predetermined events, such as washing cycles, heat treatments and similar, to which the garment has been subjected in its life.

Garments with sensors are known in the art; e.g. garments may be provided with sensors to monitor different types of parameters, e.g. the activity, of the wearer of the garments. In other known fabrics, the sensors allow to transmit signal along a garment, and to monitor vital data of the wearer. More generally, fabrics with technical yarns, such as fabrics having piezoelectric yarns, are known for, e.g., energy harvesting.

BACKGROUND

U.S. Pat. No. 6,687,523 B1 discloses a garment for infants, having an information infrastructure within the fabric that can include materials for sensing one or more body vital signs of the wearer. The information infrastructure component can consist of either a high or a low electrical conductivity component or both high and low conductivity fibers. They can be used to monitor one or more body vital signs including heart rate, pulse rate, temperature, and oxygen saturation (pulse ox), through sensors on the body and for linking to a personal status monitor (PSM). The conductive materials can be inserted within the fabric in different ways, e.g. they can be woven or knitted within the fabric.

U.S. Pat. No. 6,727,197 discloses a knitted, woven, or braided textile ribbon including one or more transmission elements. The transmission elements are preferably separated one from the others by non-conductive fibers. The transmission elements can be woven or knitted with the non-conductive fibers, and they are used to transmit signals in order to e.g. interconnect two electronic devices on the same garment, or one electronic device on the garment and a second electronic device located on another garment or a belt. In other words, the ribbon is used as a BUS.

A problem of some fabrics, especially fabrics with sensors or technical yarns, is that they might be damaged if subjected to unsuitable or inappropriate treatments such as washing cycles at too high temperatures or by dry cleaning instead of water (or vice versa), etcetera. Similarly, damages can occur when the garment is worn in unsuitable or inappropriate wearing conditions, such as in the rain or snow. Damages may also be accidental, such as a fall in the water or ironing, and similar.

In other cases, the damage develops after a certain number of events, e.g. after a number of home washings. The damage may not always be visible at first sight, in particular if only the sensors or technical yarns are damaged. As a result, the real condition of a garment may not be known by a user.

There is thus the need to find a way to detect the conditions of a garment or of a fabric. In particular, with the information obtained a user may e.g. better manage its garment, evaluate the value of used garments, etc.

Furthermore, when a fabric is damaged, thanks to this data it may be possible to evaluate if the damage is due to a poor quality of the fabric, or to a bad handling of the garment itself, e.g. because it has been cleaned too frequently and/or at a too high temperature, or in the wrong way. Other garments, e.g. work clothes, can be certified for a certain number of washings only, i.e. some properties are lost after a certain number of washings.

There is thus the need to evaluate the nature and possibly also the number of predetermined events carried out on a garment.

SUMMARY

These and other objects are achieved by means of a fabric, an article (e.g. a garment) and a process for monitoring the life-cycle of a garment according to the independent claims. Preferred aspects are listed in the dependent claims.

According to an embodiment, a fabric comprises at least one conductive element to define at least one portion of an electric circuit, and a sensor coupled to said conductive element, wherein the sensor comprises a degradable element. The degradable element is configured to at least partially degrade in preset conditions to change an electric feature of the sensor.

A "degradable element" of the sensor is an element that has at least one feature that progressively (and non-reversibly) changes in predetermined conditions, affecting at least one electric characteristic of the sensor.

In an exemplary embodiment, the degradable element can be e.g. a water degradable element. The water degradable element is configured so that an electric feature of the water degradable element is progressively changed, e.g. the dimension or the mass of the degradable element is progressively lowered (i.e. it "degrades") every time the fabric is washed. This can be achieved in different ways known in the art. As an example, the water degradable element can undergo hydrolysis so that, in contact with water, part of the degradable element is eroded. As an alternative, the water degradable element can be water soluble.

Such a water degradable element can be used to monitor the number of washing cycles carried out on a fabric provided with such a degradable element. In fact, every time the fabric is washed, the degradable element reduces its dimensions (preferably a small percentage of its total dimensions) and thus an electric feature of the electric circuit to which the degradable element is coupled is changed. As an example, a water degradable element interposed between two conductive yarns can act as a resistor. When the fabric is washed, the dimensions of the water degradable element are reduced. As a result, the resistance between the elements changes in a measurable manner (it is typically raised in a step-like manner). This changing can be used to indicate the occurrence of a washing cycle.

Also, a water degradable element may substantially maintain its dimension (or better its "external" dimension), while losing part of its content. As an example, a water degradable carrier may be filled with a degradable filler and, upon contact with water, is eroded or dissolved without substantially changing its dimensions. More in general, a water degradable element may be configured to lose (at least) part of its content (i.e. to lose mass and/or fillers) at contact with water, so that an electric feature of the electric circuit is changed.

As a further example, a piezoelectric element can be used as a "degradable element". As known, piezoelectric elements generate an electric signal when they are subjected to mechanical stimulation. The strength of the electric signal is function of the structure of the piezoelectric element, and in particular it is proportional to the polarization of the piezoelectric element. The internal structure (and thus the polarization) of a piezoelectric element can be changed e.g. by applying a certain temperature to the piezoelectric element. The material of the piezoelectric element can thus be chosen so as to lose polarization when subjected to a predetermined temperature, e.g. the one corresponding to a washing cycle for the fabric. As a result, when the fabric is washed at a certain temperature, the polarization of the piezoelectric element is changed. The change can occur once or in several times. As before, this degradation of the piezoelectric element will result in a change of the signal of the sensor incorporating said piezoelectric element and can be used to show the occurrence of a heat treatment.

According to an embodiment, the fabric is a woven or knitted fabric, and the conductive elements are conductive yarns that are inserted within the fabric, i.e. they are part of the woven or knitted structure of the fabric. As a result, the yarns can be easily implemented in the fabric. Also, the external appearance of the fabric is not particularly affected by the presence of the conductive yarns. As above mentioned, according to preferred embodiments, the degradable element is configured to partially degrade during a cleaning cycle or a heat treatment carried out on the fabric.

These events are particularly relevant in the life of garments. Thanks to the present embodiment, it is possible to monitor the occurrence of a cleaning cycle and/or a heat treatment. It should be noted that in some circumstances these two events can coincide, or in any case they can be carried out at the same time. As an example, a washing machine can use hot water. As a result, a washing machine can perform contemporarily a cleaning cycle and a heat treatment.

In a further embodiment, the "life" of the degradable element can be made equal to the expected life of the fabric/garment. As an example, if a garment is supposed to be discarded and no longer used after, e.g. 100 cleaning cycles, the degradable element can be configured to have a feature that degrades about 1%, or e.g. 0.5% at every cleaning cycle. As a result, during the "working life" of the degradable element actual degradation of the degradable element can be used e.g. to show the remaining expected life of the garment. When the feature measurable through the degradable element is no longer present or has reached a pre-set value (i.e. 0% or 50% in the above cited examples), by this fact it is shown that the garment needs to be replaced by a new one.

As mentioned, according to an embodiment, the degradable element is water soluble. As a result, the degradable element reduces its dimension/mass every time it comes in contact with water. In another embodiment, the element is a polymer that is partially hydrolyzed in water and that contains a filler, such as carbon powder or graphene, that makes the filled polymer a resistive element; some of the polymer matrix and of the filler is lost at each washing so that the initial value of the element's resistance changes with each washing.

Preferably, a water degradable element is configured so that, during a normal washing cycle, only a small portion of the degradable element is lost (e.g. it is eroded or taken away).

This result can be obtained by a proper dimensioning of the water degradable element, and/or by properly choosing the material(s) of the water degradable element.

According to an embodiment, the degradable element is a resistor interposed between two conductive elements. In particular, a (water) degradable element can be interposed between two conductive elements and acts as a resistor. As before mentioned, a water degradable resistor reduces its dimensions/mass every time it is washed. As a result, the electric resistance of the degradable element is raised at every washing cycle.

Suitable materials for implementing degradable resistors are known in the art and are e.g. polyethers, polycaprolactone (PCL), polylactic acid (PLA), thermoplastic polyurethanes (TPU); conductive fillers and also magnesium and silicon may be used with the polymers.

In a different embodiment, a degradable element, preferably a water-degradable element, is interposed between two conductive elements, so as to form a capacitor. In particular, the degradable element acts as the dielectric portion of the capacitor.

The water degradable element changes, e.g. its mass or volume or its dimensions are reduced every time it is washed. As a result, the capacitance of the capacitor formed by the conductive elements and by the degradable element is changed, at every washing cycle. Suitable materials for degradable capacitors are e.g. aliphatic polyisocyanate, cross-linked polyether and polyester polyols resulting in stretchable polyurethanes.

In another embodiment, a conductive element, e.g. a conductive yarn, is wound around a water degradable element to form an inductor coil, and the degradable element can be the core of the inductor. As a result, the inductance of the inductor formed by the conductive elements and by the degradable element is changed, e.g. lowered, at every washing cycle. Suitable materials for degradable inductors are known in the art and are e.g. polycaprolactone (PCL), polylactide (PLA), and thermoplastic polyurethanes (TPU).

As per before, the water degradable element reduces its mass or dimensions every time it is washed. As a result, the inductance of the inductor formed by the conductive element and by the degradable element is changed at every washing cycle.

More in general, passive electric circuital elements (resistors, capacitors, inductors, memresistor and so on) can be used as degradable sensors, when they are provided with an element that is capable of changing an electric feature of the electric element when subject to a preset condition, typically by reducing its dimension (or more in general its mass) when contacted with water.

Preferred materials for sensors having a degradable element that reduces its mass/dimensions when washed were recited above. Materials suitable to be used are e.g. a Poly-Ether-based matrix materials having conductive carbon impurities (carbon black, carbon powder, carbon nanotubes, graphene, etc.) dispersed therein.

According to a different embodiment, the degradable element comprises a piezoelectric element. In particular, piezoelectric elements are "degradable" when subject to heat. In particular, the piezoelectric element can change its structure, so as to lose polarization when heated at certain temperatures; loss of polarization is preferably a progressive loss. As mentioned, the piezoelectric element can be configured (e.g. by a proper choice of materials) to lose polarization at temperatures substantially equal to the ones required during a washing cycle. As a result, during a washing cycle, if the fabric is heated, the piezoelectric element loses polarization; in general polarization is lost substantially completely after the first event has occurred, so that the sensor is of the once-only type. In other embodiments, polarization may be lost gradually, by several steps and the sensor generates each time a signal lower than the signal before the washing cycle (i.e. the heat treatment occurred during the washing cycle).

According to an embodiment, the piezoelectric sensor comprises a piezoelectric sheet, preferably an electro-spun material such as a polyvinylidene fluoride (PVDF) or a polymer of the same family, that is sandwiched between two conductive (e.g. aluminum) sheets. The conductive sheets are preferably connected directly to an analog to digital converter of the controller with pull-up/down resistors.

According to an embodiment, the degradable element can show that the garment has been used and that the garment has been washed. To this purpose, the degradable element is configured to provide a first degree of degradation when the fabric is worn by a user and a second degree of degradation at a washing cycle or a heat treatment. Preferably, the second degree of degradation is greater than the first degree of degradation. When monitoring the degradation of the degradable element (e.g. by means of a controller), it is possible to distinguish the first and the second degree of degradation, to acknowledge the occurrence of the relevant event.

In other words, a sensor comprising a degradable element can be used to monitor and distinguish the occurrences of different kinds of events.

As an example, a water degradable element may be slowly eroded by hydrolysis and in a very small percentage during normal use, e.g. because of the sweat, or in general contact with the skin, of a user. On the contrary, during a washing cycle, a water soluble degradable element can degrade faster and in a greater percentage than during use.

According to an embodiment, the degradable element is provided with a third degree of degradation at an undesired event, different from the preset condition.

As an example, heating at a too high temperature can cause a substantially complete de-polarization of a piezoelectric element, so that it stops generating an electric signal. Thanks to this, it is possible to know that a too aggressive heat treatment has been carried out on a fabric, or on the garment. Similarly, a sudden and great loss of dimension of a water soluble element can indicate that a too aggressive cleaning cycle has been carried out.

An embodiment of the present invention provides for an article, such as a garment, comprising a fabric according to any of the preceding aspects. In a further embodiment the article comprises a controller coupled to the electric circuit to monitor the variation of the electric feature.

In other words, the controller checks if an electric feature of the electric circuit, such as a signal from the sensor, changes over time, as a result of the degradation of the degradable element.

This check can be continuous or at discrete time intervals. As an example, the controller can send an electric signal within the electric circuit, and checks, e.g. the resistance/capacitance/inductance of the electric circuit at the degradable element. Otherwise it can receive and evaluate the electric signal received e.g. from a piezoelectric element.

According to an embodiment, the controller is placed within a button of the garment. Thanks to this, the garment can be provided with both a sensor (i.e. the circuit with the degradable element) and with means (i.e. the controller) to receive and evaluate the signals from the sensor.

An aspect of the present invention further provides for a process for monitoring the life-cycle of a fabric or of a garment according to one or more of the preceding aspects. In particular, the process comprises the steps of:
  (a) providing a fabric with at least one conductive element to define at least one portion of an electric circuit, and a sensor coupled to said conductive element, said sensor having a degradable element configured to partially degrade in preset conditions, whereby degradation of said element changes an electric feature of said sensor;
  (b) monitoring and storing said electric feature;
  (c) evaluating the value of degradation of said electric feature and/or the number of degradation events as a function of monitored data stored in step (b);
  (d) determining the status of said fabric as a function of the evaluation at step (c).

In a preferred embodiment, the above mentioned step (c) comprises in turn the steps of:
  (c1) evaluating a function the monitored electric feature as a function of time;
  (c2) evaluating the derivative of the function of the monitored electric feature of step (c1)
  (c3) counting the peaks of the derivative function of step (c2), wherein each peak is associated to one occurrence of said event.

Typically, step (c3) is carried out if the peak is greater than a certain threshold, in order to count only the occurrences of the event.

A further aspect of the present invention relates to an electric circuit comprising at least one conductive element to define at least one portion of the circuit, and a sensor coupled to the conductive element. The sensor comprises a degradable element configured to at least partially degrade in preset conditions to change an electric feature of the sensor, and the circuit is suitable to be inserted into a fabric.

Preferably, the electric circuit is provided with conductive elements that can be placed into a fabric (e.g. they can be conductive yarns that can be used to produce the fabric, such as weft/warp yarns). Also, the degradable element is preferably of a material that can be easily placed in, or deposited onto, a fabric.

DESCRIPTION OF THE DRAWING

Exemplary and non-limiting embodiments will be now discussed with reference to the enclosed figures, in which:
FIGS. 2A, 2B, and 20 are different embodiment of water degradable elements, respectively a resistor, a capacitor and an inductor.

DETAILED DESCRIPTION OF THE EMBODIMENTS

Figure 1:
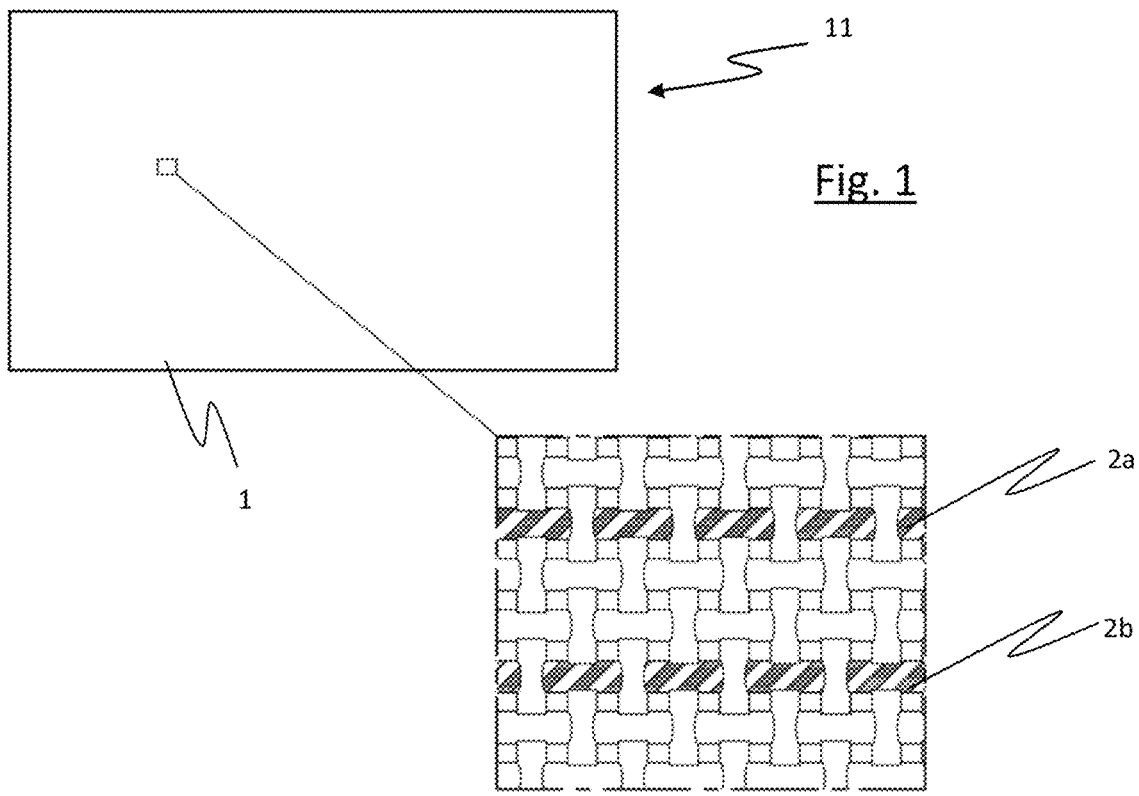
FIGS. 1 and 2 are schematic views of a fabric of embodiments of the invention.

With reference to the figures, an article 11 (shown schematically in FIGS. 1 and 2) comprises a fabric 1 which in turn comprises at least one conductive element 2 to define an electric circuit 3. A sensor 12 comprises a degradable element 4 coupled to the one or more conductive element 2. Degradation of the degradable element 4 causes a variation of one (or more) electric feature of the electric circuit 3.

Preferably, a controller 10 can be coupled to the electric circuit 3 to evaluate the variation of such an electric feature.

The fabric 1 is preferably a woven or knitted fabric. Conductive elements 2 can thus be conductive yarns 2a, 2b that are part of the woven or knitted fabric, i.e. they can be inserted in the fabric as yarns of the woven or knitted structure of the fabric itself.

In a preferred embodiment, fabric 1 is a denim fabric for trousers. In any case, fabric 1 can be a generic fabric.

Figure 2:
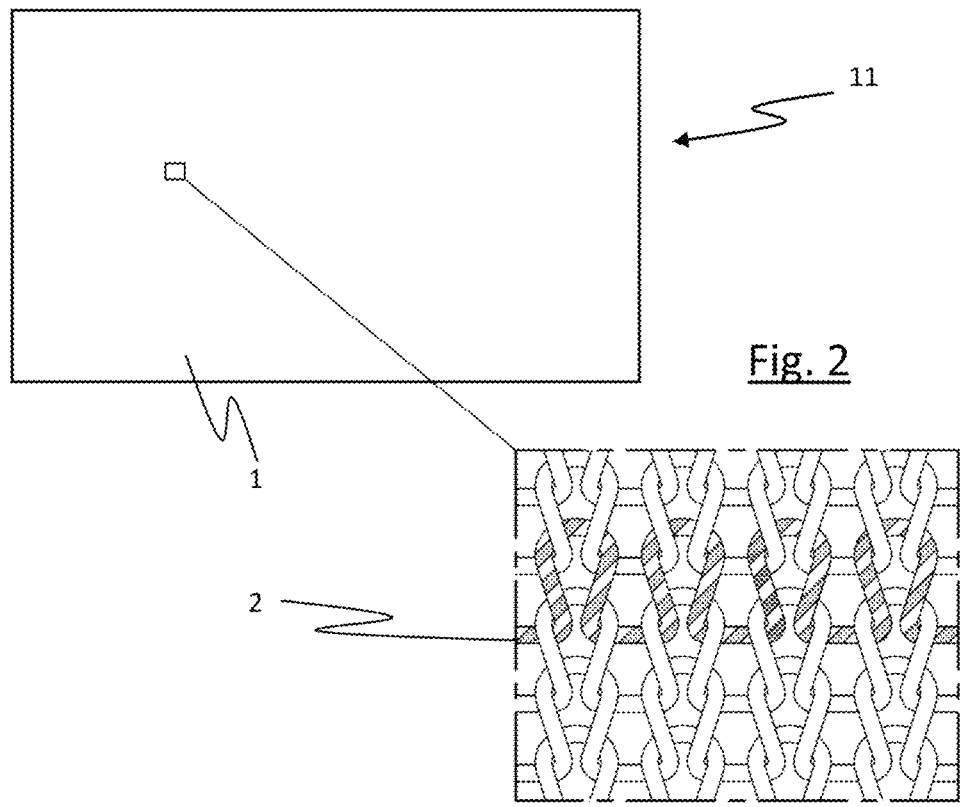
Figure 2A:
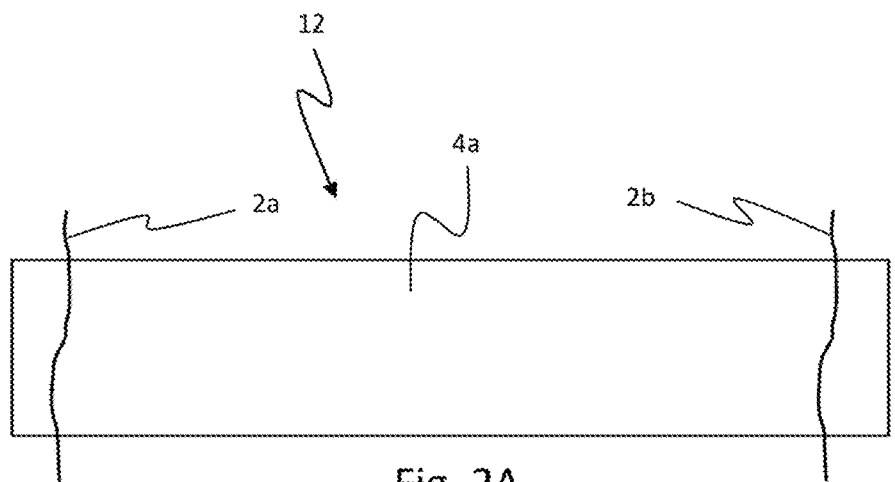
Figure 2B:
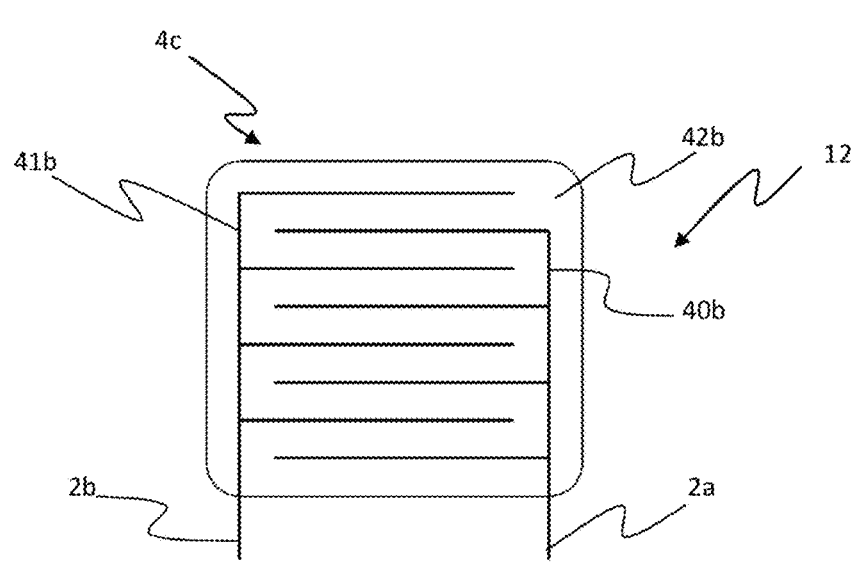
Figure 2C:
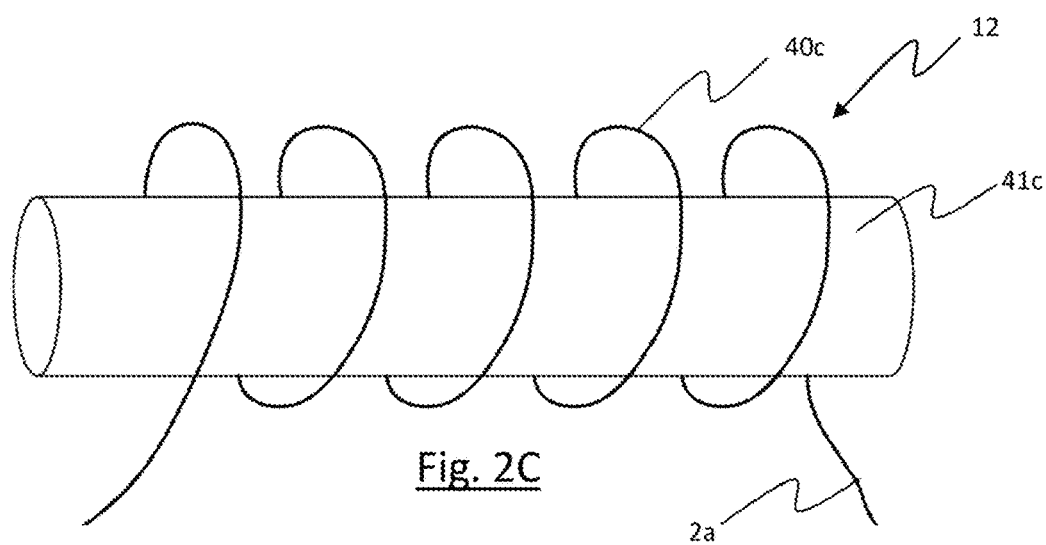

In FIG. 1, two conductive yarns 2a, 2b in a woven structure of a fabric 1 are shown. In FIG. 2 a conductive yarn 2 in a knitted structure of a further fabric 1b is shown.

Conductive yarns can comprise e.g. steel or copper or silver wires, and they can be e.g. monofilament, or they can be blends of multiple fibers forming the final yarn.

Alternative conductive elements can be used. In the exemplary embodiment of FIG. 6, two metal elements 2c coupled to the fabric are used as a conductive element.

According to a further embodiment, shown in FIG. 6B, snaps 2e (typically male snaps) may be crimped to conductive elements 2a, 2b (e.g. steel yarns)—shown in dotted lines—to provide ohmic contacts with the latter, so that they may be connected (e.g. via standard female snaps) to an external circuitry, e.g. to download data recorded by the controller to an external data processor.

In general, conductive elements allow transmission of an electric signal along a portion of the fabric. In more detail, conductive elements are coupled to degradable elements, so as to form a portion of an electric closed path.

In more detail, the conductive element(s) 2, 2a, 2b, 2c is/are disposed within/coupled to the fabric 1 so as to form a closed path, i.e. an electric circuit 3, preferably together with the controller 10. The controller 10 can be inserted within the fabric 1, or it can be an element external to the fabric 1.

As an example, a controller 10 can be inserted within a button which is configured to be coupled to the fabric, as disclosed in pending application EP 15179147.2 in the name of the present applicant. The conductive elements(s) 2, 2a, 2b, 2c is/are disposed so as to close an electric path with the external controller 10, when the latter is coupled to the fabric 1 in the final garment. The electric controller 10 comprises known means to generate and/or evaluate an electric signal, and to monitor an electric feature of the electric circuit 3.

Figure 3:
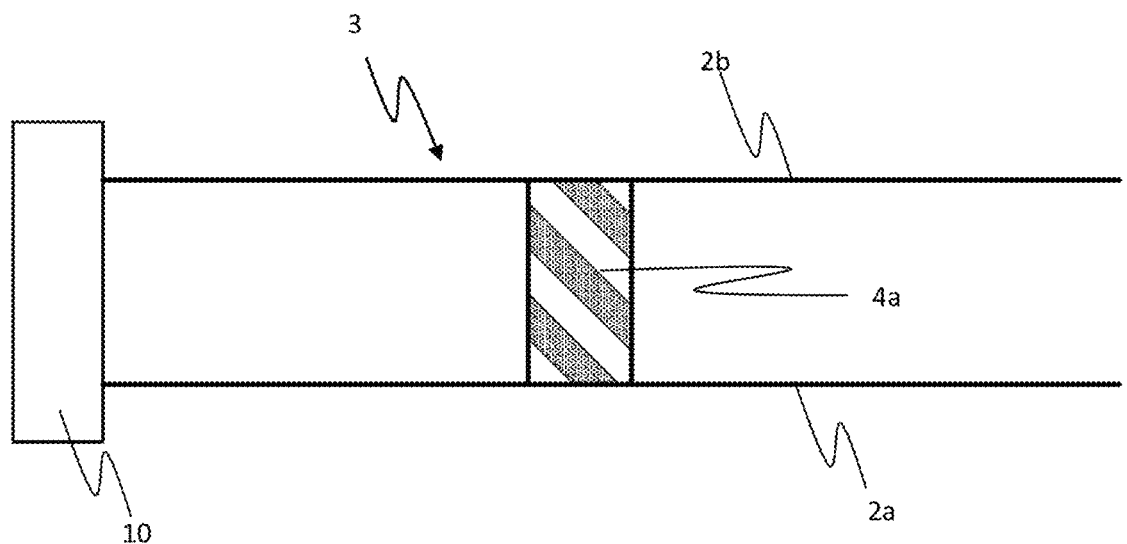
FIG. 3 is a schematic view of an electric circuit comprising a water degradable resistor according to an embodiment of the invention.

As an example, in FIG. 3 an electric circuit 3 in a schematic and simplified view is shown.

The electric circuit 3 comprises two conductive yarns 2a, 2b. The yarns 2a, 2b can be inserted within the fabric 1 as per above disclosed. The fabric 1 is not shown for clarity. A degradable element 4a is interposed between the yarns 2a, 2b. The electric circuit is closed by a controller 10.

The electric circuit 3 may be more complex than what shown. As shown for example in FIG. 11, the circuit 3 can comprise an analog-to-digital converter (ADC) 5, to allow the controller 10 to manage a digital signal, as better discussed later.

According to an embodiment, the electric circuit 3 can comprise a pull-up or pull-down resistance 7, to avoid short circuits and to limit external disturbances. In general, the sensor 12 is able to generate a signal towards and/or from the degradable element 4, for example a degradable resistor 4a as per FIG. 11. In particular, the electric circuit 3 is generally configured to allow transmission of a signal between the degradable element 4 and the controller 10.

Figure 11:
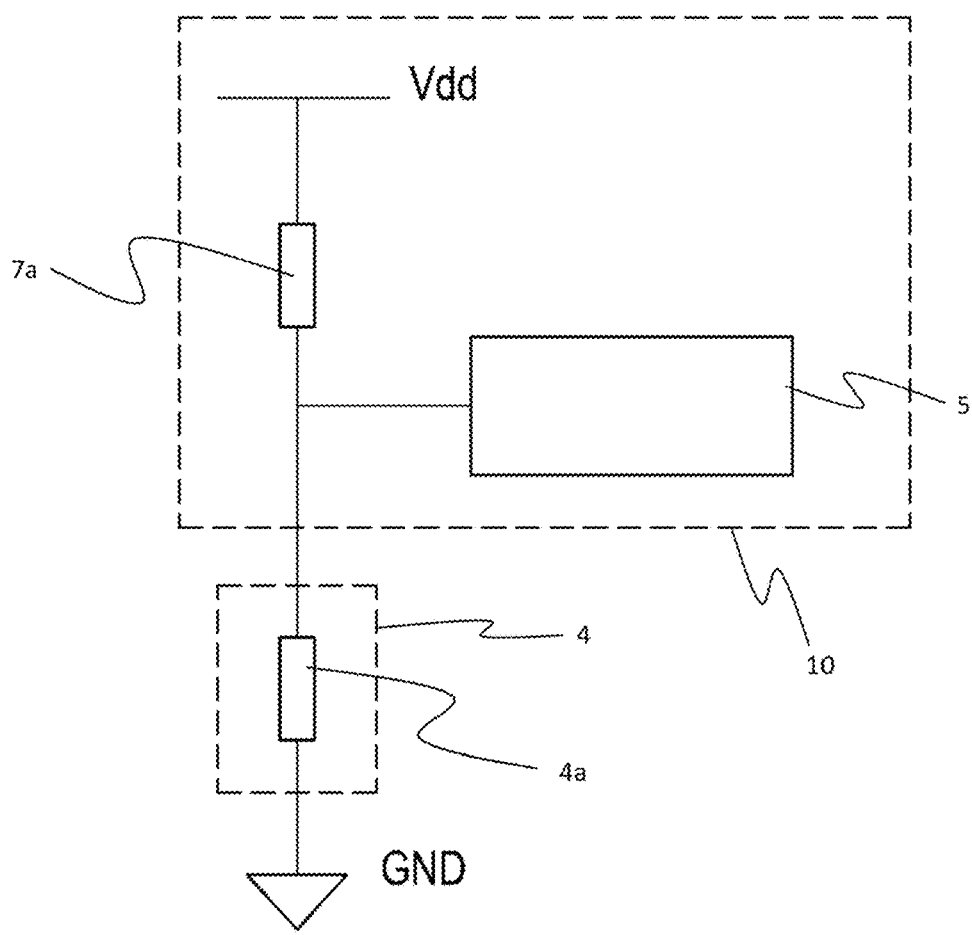
FIGS. 11, 11A, 11B are schematic views of electric circuits of further embodiments of the invention.

In the particular embodiment of FIG. 11, the sensor comprises a degradable resistor 4a, and a further resistor 7a arranged in series with respect to the resistor 4a, so as to form a voltage divider. According to an aspect, the resistance value of the resistor 7a may be chosen as follows.

R_ini being the initial value of the resistance of the resistor 4a (i.e. before any degradation) and R_fin being the larger expected final resistance value of the resistor 4a at the end of its operative life time, the voltage divider resistor 7a has preferably a resistance value R_div defined by the geometric average of R_ini and R_fin. In other words the value of the resistance of the voltage divider resistor 7a can be chosen as per the following formula:

$$R_{div} = \sqrt{(R_{ini} * R_{fin})}$$

The above mentioned preferred value of the voltage divider resistor 7a guarantees the maximum dynamic range at the input of the ADC 5. The above disclosed voltage divider is particularly useful during measurement the resistance value of the resistor 4a.

Figure 11A:
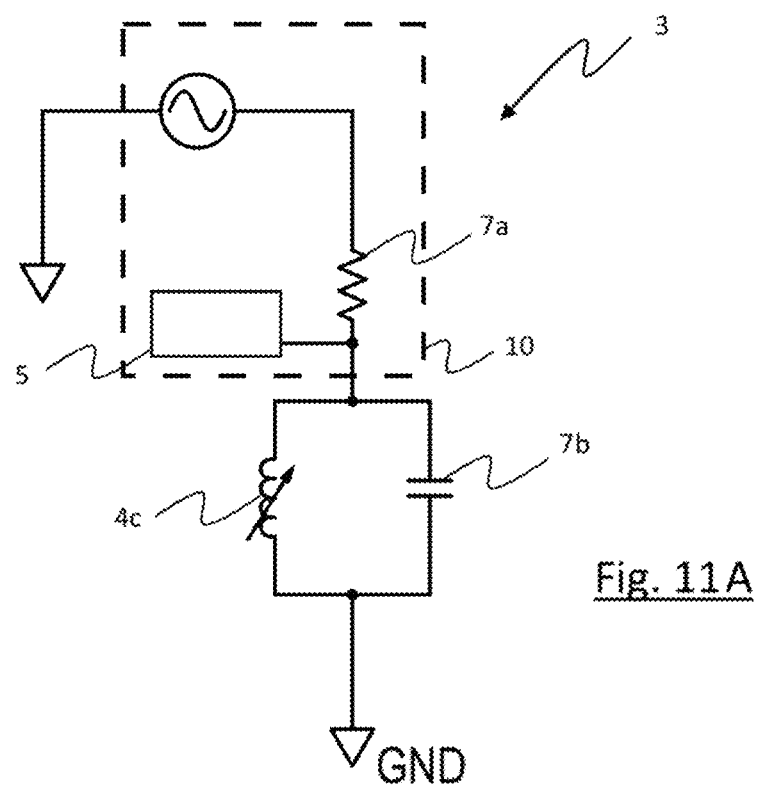

A resistor 7a may be used to form a voltage divider also in combination with a degradable sensor having a degradable inductor 4c, as shown in FIG. 11A. In this case, the degradable inductor 4c (better discussed later) is preferably arranged in parallel with respect to a non-degradable capacitor 7b.

Figure 11B:
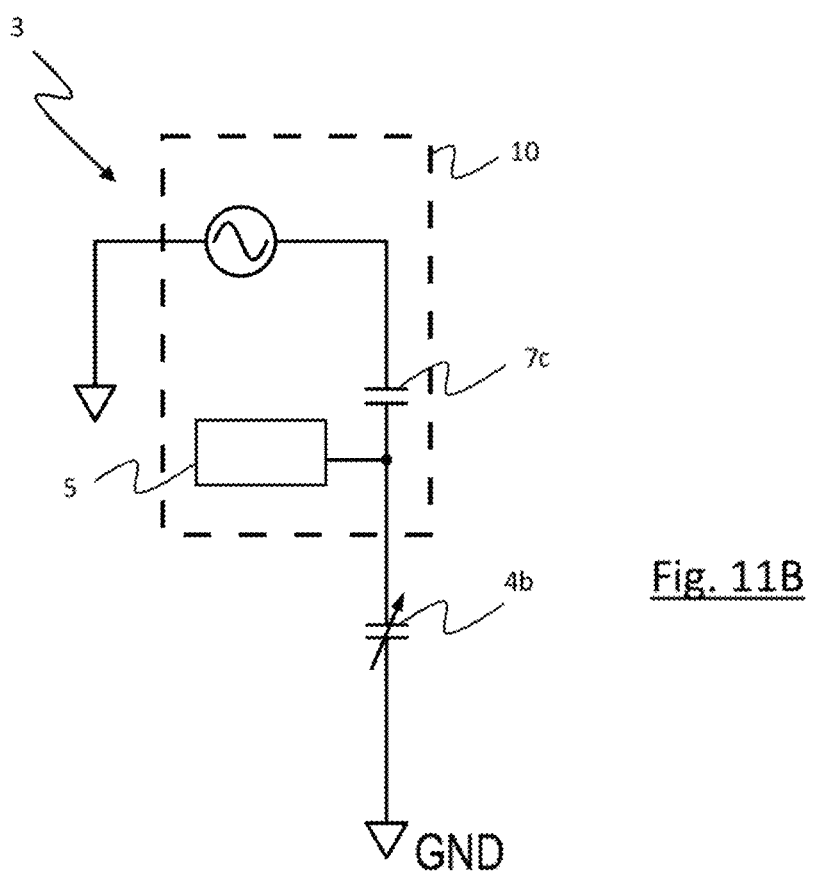

Also, a voltage divider may be used without a (pull up/pull down) resistor, as shown in FIG. 11B, where a capacitive voltage divider is shown, wherein a degradable capacitor 4b is put in series with a reference capacitor 7c.

Figure 9:
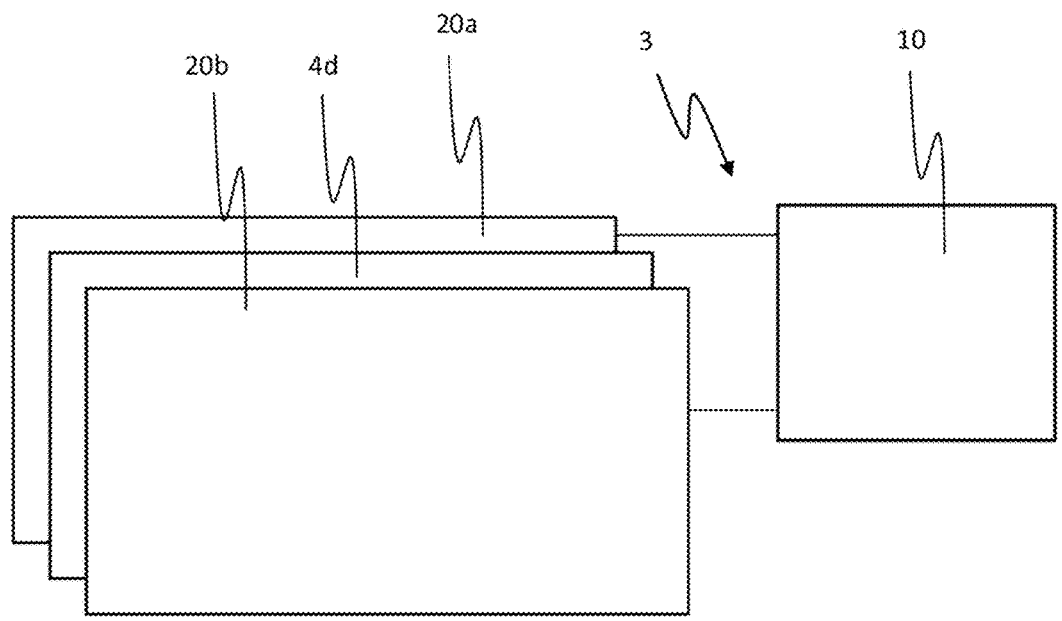
FIG. 9 is a schematic view of an electric circuit comprising a piezoelectric degradable element according to an embodiment of the invention.
Figure 9A:
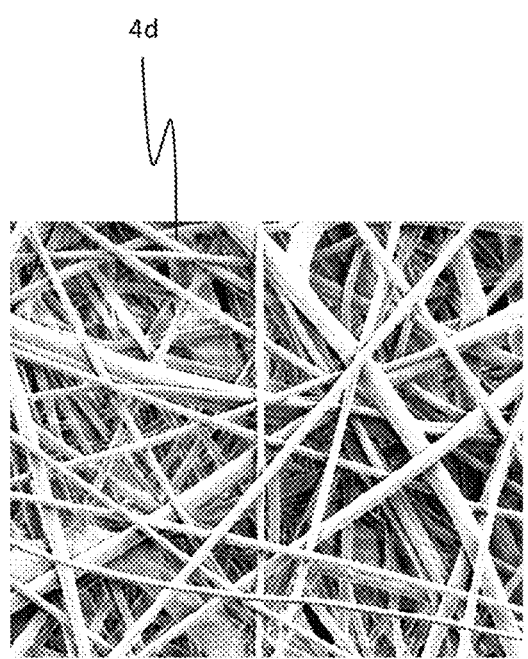
FIG. 9A is a SEM image of a piezoelectric degradable element of the embodiment of FIG. 9.
Figure 9B:
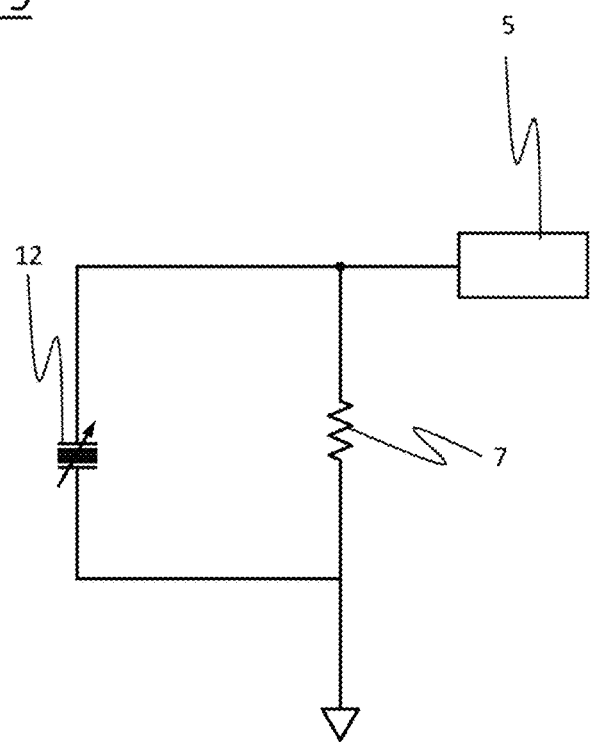
FIG. 9B is a schematic view of a further electric circuit with the sensor of FIG. 9.

A pull up/pull down resistor 7 is also shown in combination with a degradable piezoelectric sensor in an exemplary embodiment in FIG. 9B. In this case the value of the resistance of the pull up/pull down resistor 7 can be chosen with more freedom as it is not used in a voltage divide together with a degradable resistor as per FIG. 11.

Figure 14:
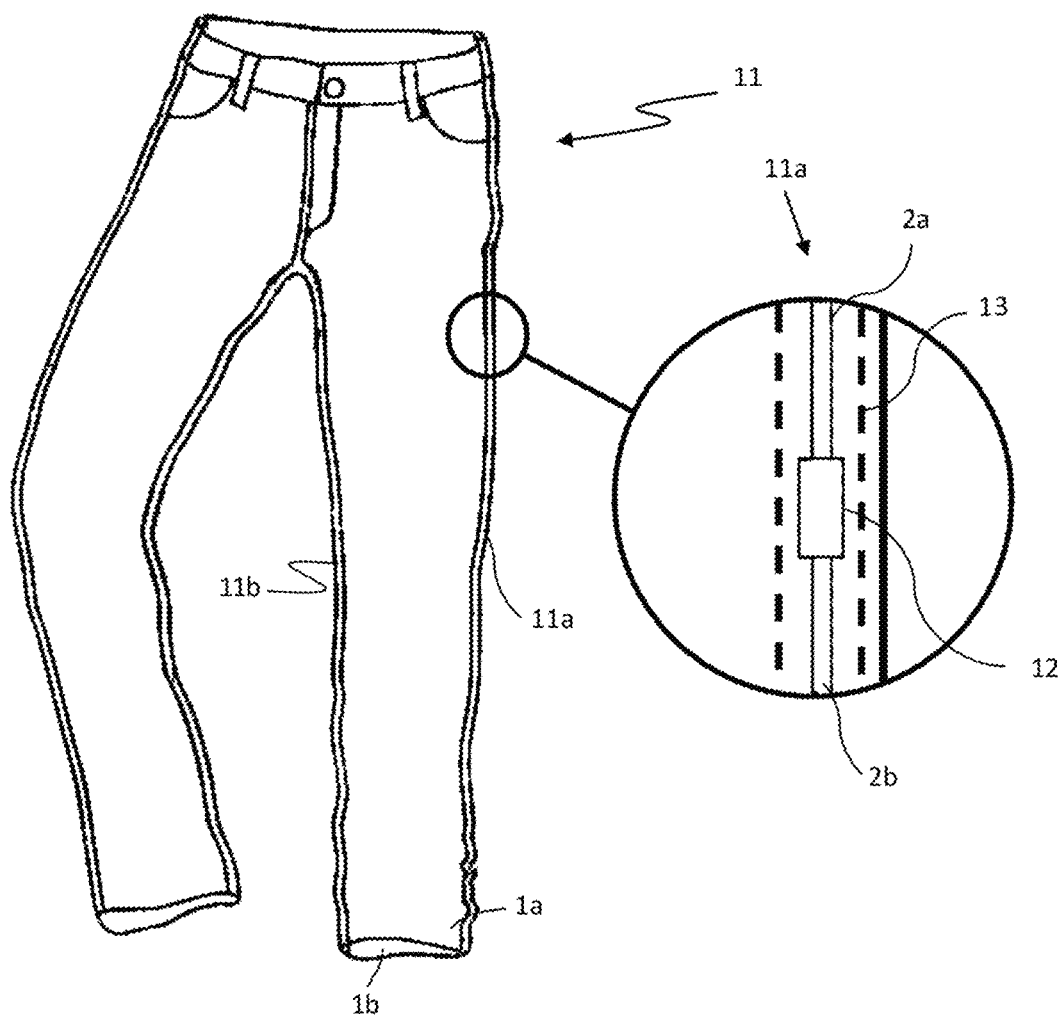
FIG. 14 shows a denim article with a sensor in the seams.

According to an embodiment, the sensor 12 can be placed within seams 11a, 11b of the article 11 (see FIG. 14), so that the sensors 12 are not visible when looking at the article, i.e. they are hidden within the seams. In other words, the sensors 12 may be surrounded by fabric and be placed inside a seam 11a. As used herein, a seam 11a, 11b is a portion of an article 11 in which two overlapping portions of fabric(s) are joined together. A close-up of a seam 11a is schematically shown in FIG. 14. Seam 11a shown in FIG. 14 represents one seam embodiment but various types of seams are used in other embodiments. Various stitching types and other methods may be used to form seams in other embodiments. In the shown embodiment, the article 11 is a pair of denim jeans but other materials as well as different articles can be used in other embodiments. As an example, article 11 may be an item of apparel worn by a wearer including but not limited to shorts, a shirt, a full body suit, sleeves for legs and arms and the like.

FIG. 14 shows seam 11a formed of two fabric pieces 1a, 1b that are joined together to form seam 11a by stitchings 13. A sensor 12 is placed within the seam 11a, and it is connected to conductive elements 2a, 2b that at least partially run within the seam 4.

In particular, FIG. 14 shows an article 11, namely a garment, which is a pair of denim pants. In other embodiments according to various aspects of the disclosure, the article may be a different garment, e.g. a piece of apparel such as may be worn by a user. In the illustrated embodiment, the article 11 includes seams 11a, 11b, at least at outer lateral locations (seam 11a) and medial internal locations (seam 11b) on each pant leg. Seams 11a, 11b generally extend along the longitudinal direction of a wearer's legs and are therefore generally parallel to the wearer's femur in the upper portion of the pant legs, and parallel to the wearer's tibia and fibula in the lower portion of the pants leg, when the article 11 is worn by a wearer.

Furthermore, even if not shown in detail, further seams may be provided on the article 11, e.g. at the top portion of the pants, i.e. at the portion of the pants usually configured to house a belt. The sensor 12 may be placed within any of these seams, according to the needs. It is further noted that seams 11a, 11b are used to produce the article, so that the sensor can be placed within a pre-existing seam of the article. Such a seam may be provided with an area having greater dimension (e.g. greater width) with respect to the other areas of the seams, in order to house a sensor in the greater area. Also, in some embodiments, a sensor may be placed within a seam that is created ad hoc for the sensor. In other words, a seam that have no "structural" function can be provided on the article with the only purpose to house a sensor. A seam may be thus formed on an article in order to form a "pocket" where a sensor may be housed.

Also, the controller 10 can be placed within a seam 11a, 11b of an article 11. The controller 10 can be connected to the sensor by means of conducting elements (e.g. conducting yarns such as steel yarns) that do not degrade.

As before mentioned, various kinds of degradable elements can be used in different embodiments of the present invention. Embodiments with water degradable elements and piezoelectric elements will be now discussed in detail.

With reference to FIG. 3, a water degradable resistor 4a is interposed between two conductive yarns.

The water degradable resistor 4 is preferably made of polyether and/or polyester based polyurethanes.

Figure 3A:
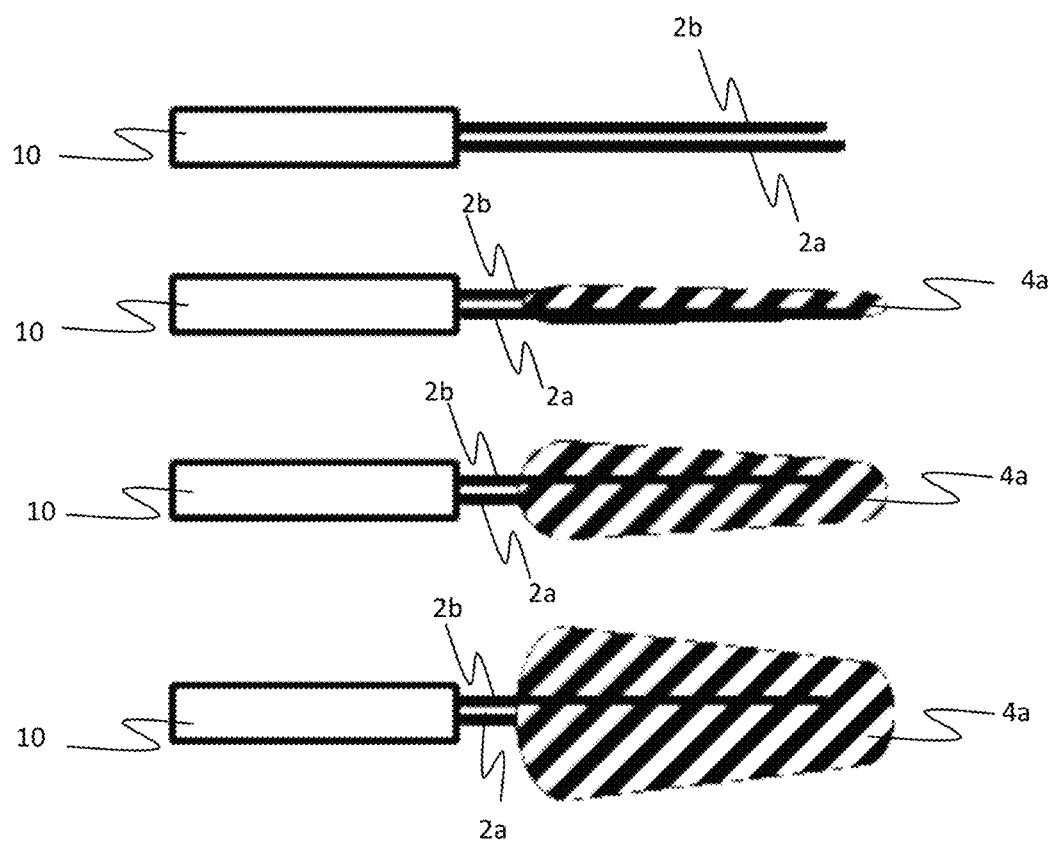
FIG. 3A is a schematic view of the progressive degradation of a water degradable resistor according to an embodiment of the invention.

The water degradable resistor 4a partially reduces its mass/dimensions each time the fabric 1 is washed. This is schematically shown in FIG. 3A. In particular, degradation of the water degradable resistor is shown from bottom to top of FIG. 3A. In more detail, at the bottom of FIG. 3A a complete water degradable resistor is shown. At the top, the water degradable resistor 4a is completely degraded. Between the bottom and the top portion of FIG. 3A intermediate conditions are shown.

Each time the water soluble resistor reduces its mass/dimension, i.e. each time the water soluble resistor loses part of its material, the relevant electric feature (i.e. the resistance) is changed.

A water degradable resistor (and more in general a water degradable element, as the water degradable elements 42b and 41c subsequently discussed) is preferably configured to vary the relevant electric feature (e.g. resistance in the present case of a resistor) of about 1% to 5% at each washing cycle. As mentioned, in fact, the resistance of the resistor 4a is dependent on the mass/dimensions of the resistor 4a itself. In particular, the resistance increases with a decrease of the mass/dimensions of the resistor 4a. In fact, when the resistor loses mass (both by a reduction of the external dimension of the resistor, or by losing a filler of the resistor), the electric path that is traversed by the electric current narrows, thus raising the resistance of the resistor.

As better discussed later, a change in the resistance of the resistor 4a in the sensor 12 can be sensed by the controller 10, in order to evaluate the life-cycle of the fabric 1, and in particular to evaluate the history of washing cycles on the fabric 1.

Figure 4:
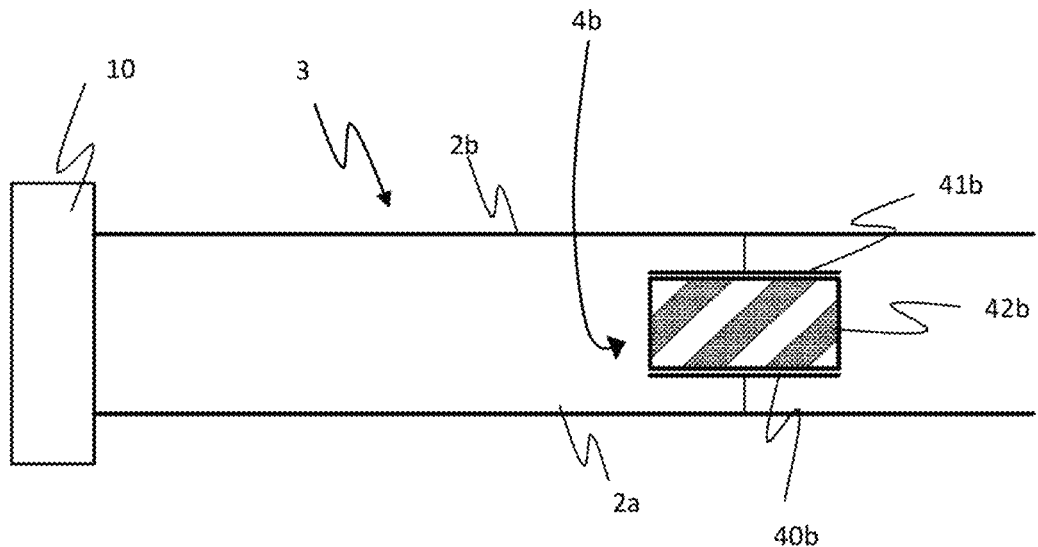
FIG. 4 is a schematic view of an electric circuit comprising a water degradable capacitor according to an embodiment of the invention.

Water degradable elements can be used not only as a resistor. As an example, in FIG. 4, an embodiment is shown wherein a water degradable element is used in a capacitor 4b. In particular, the capacitor 4b comprises a portion 40b, 41b of two conductive yarns 2a, 2b (i.e. one portion 40b of a first conductive yarn 2a and one portion 41b of a second conductive yarn 2b). A water-degradable dielectric portion 42b is interposed between the two portions 40b, 41b, so as to form a capacitor 4b. As before, during a washing cycle, the dielectric portion 42b partially reduces its mass/dimensions, and thus the capacitance of the capacitor 4b is changed, e.g. lowered.

Figure 5:
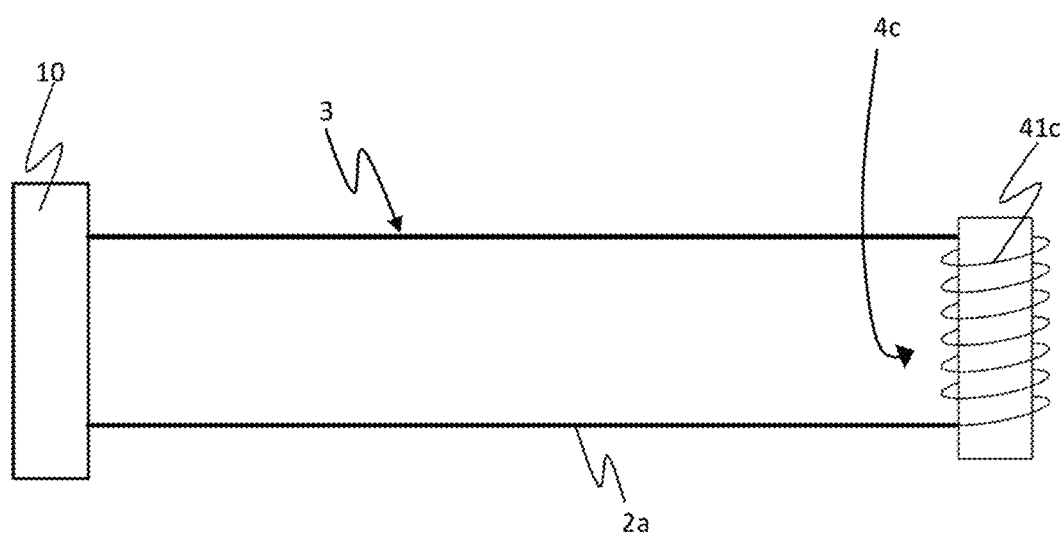
FIG. 5 is a schematic view of an electric circuit comprising a water degradable inductor according to an embodiment of the invention.

In a further embodiment, shown schematically in FIG. 5, a degradable element is used as the core 41c of an inductor 4c. In more detail, one portion 40c of a conductive yarn 2a is wound around a water degradable core 41c, so as to form an inductor 4c.

During a washing cycle, the water degradable core 41c partially reduces its mass/dimensions, so that the inductance of the inductor 4c is changed, e.g. lowered.

More in general, different water degradable elements can be used in different embodiments of the present invention, provided that the partial degradation (e.g. by erosion caused by hydrolysis) of the water degradable element causes a sensible variation within the electric circuit 3, i.e. it changes the value of an electric features of the electric circuit 3.

In the above disclosed embodiments, the "electric feature" changed by the water degradable element are respectively the resistance (in FIG. 3), the capacitance (in FIG. 4) and the inductance (FIG. 5) of the electric circuit 3 at the relevant water degradable element 4a, 42b, 41c.

As mentioned, the conductive elements are not limited to conductive yarns.

Figure 6:
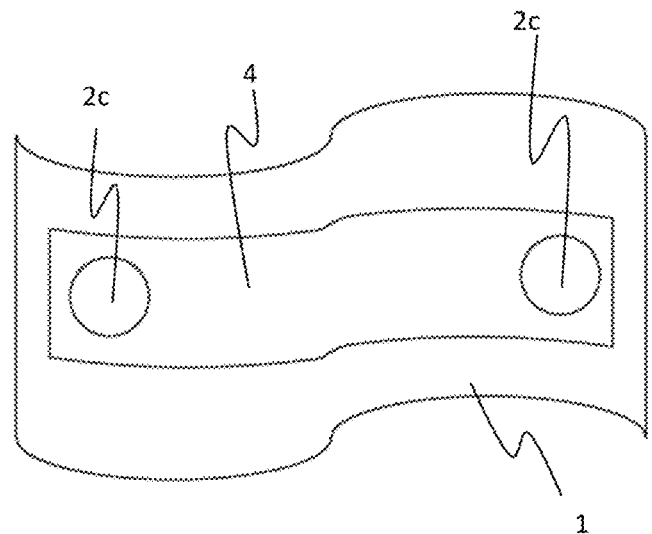
FIG. 6 is a schematic view of a degradable element according to a further embodiment of the invention.
Figure 6A:
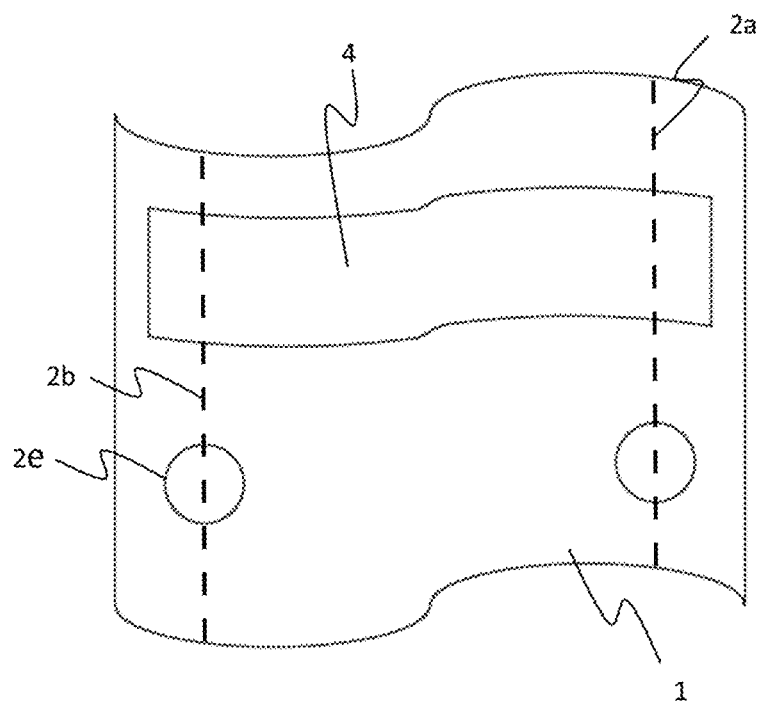
FIG. 6A is a schematic view of an alternative embodiment of FIG. 6.

With reference to the embodiment of FIG. 6, a water degradable element 4 is interposed between two metal elements 2c coupled to the garment, e.g. they can be parts of a metal button.

In particular, the degradable element 4 connects the two metal elements 2c so as to allow transmission of an electric signal between the metal elements 2c.

Such an electric signal can be generated by a controller 10 (not shown in FIG. 6), e.g. embedded in a further button (not shown).

Water degradable elements were disclosed. However, different degradable elements can be configured to reduce their mass/dimensions when put in contact with different fluids (i.e. other than water), e.g. tetrachloroethylene, or other solvents used in dry cleaning. Moreover, in further embodiments of the present invention, degradable elements 4 that do not reduce their mass/dimensions when they are put in contact with a liquid can be used.

As an example, in FIG. 9, a piezoelectric degradable element 4d is shown. In particular, in the shown embodiment, a piezoelectric degradable element 4d can be formed as a layer interposed between two conductive layers 20a, 20b (other conductive elements can be used as well together with a piezoelectric degradable element).

The piezoelectric degradable element 4d of the embodiment is made of a polyvinylidene difluoride (PVDF), in particular, of a semi-crystalline poly(vinylidene fluoride) polymer. The piezoelectric degradable element 4d generates an electric signal when it is subjected to mechanical stimulation, e.g. when the fabric carrying the piezoelectric degradable element is bent, stretched, pressed, wrinkled, sheared, stressed, released/relaxed, etc.

A SEM (scanning electron microscope) image of a PVDF family member is shown in FIG. 9A. In FIG. 9B a piezoelectric sensor 12 is shown in an electric circuit, wherein the sensor (in particular the conductive layers) is connected directly to an analog to digital converter 5 of the controller 10 with pull-up/down resistors 7.

The strength of this signal is dependent on the polarization (i.e. the orientation of the electric dipoles 41d of FIG. 10) of the piezoelectric degradable element. Piezoelectric element can partially lose polarization (i.e. partially lose the alignment between the electric dipoles 41d) when subjected to heat. In an embodiment, the material of the piezoelectric degradable element 4d is thus chosen so as to lose polarization at temperatures reached during cleaning cycles.

As a result, when the fabric 1 is heated during a cleaning cycle (e.g. due to contact with hot water), the piezoelectric degradable element 4d partially loses polarization, and thus the strength of the electric signal generated by the piezoelectric degradable element 4d is lowered.

As before, the piezoelectric degradable element 4d can be made of a material that does not to completely lose polarization when heated during a single cleaning cycle.

In other words, the signal generated by the piezoelectric degradable element is preferably varied after a heat treatment. This variation is preferably comprised between 5% and 95%, more preferably between 10 and 50%.

Figure 10:
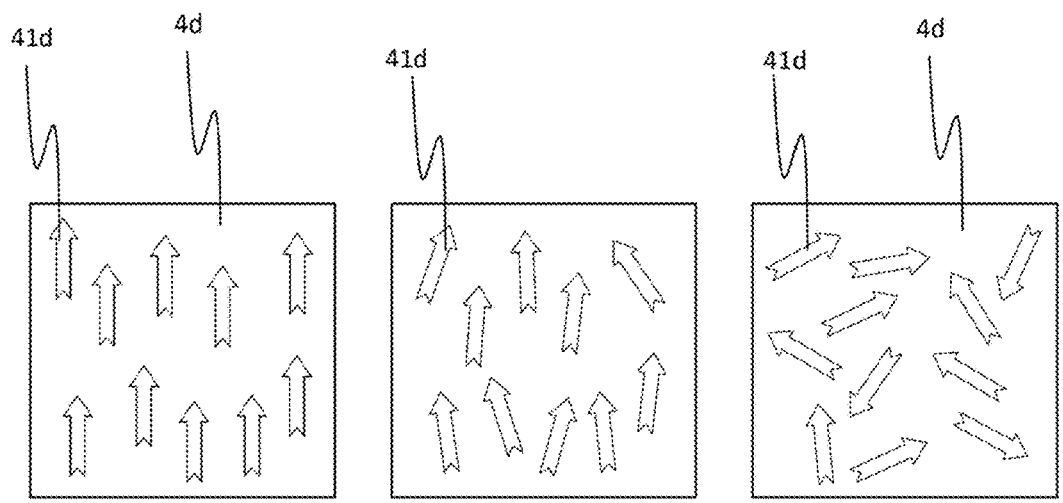
FIG. 10 is a schematic view of the progressive degradation of the piezoelectric degradable element of FIG. 9.

In FIG. 10, the "degradation" of a piezoelectric element is shown, wherein a not degraded piezoelectric element is shown at the left (i.e. a completely polarized piezoelectric element), and a completely degraded piezoelectric element is shown at the right (i.e. a completely de-polarized piezoelectric element). An intermediate condition is shown in the middle.

In other words, electric dipoles 41d of the piezoelectric degradable element 4d are completely aligned at the left, partially aligned in the middle, and not aligned at the right of FIG. 10.

The material of the piezoelectric element 4d can be chosen to allow counting of the occurrence of heat treatments. Different piezoelectric elements can be used to count the occurrences of different events, in particular heat treatments.

Different degradable elements can be used as well in other embodiments of the present invention.

In general, as mentioned, a degradable element 4 is configured to partially degrade during a preset condition, i.e. at the occurrence of a predetermined event, so as to change an electric feature of the electric circuit 3 to which the degradable element 4 is coupled.

According to further embodiments of the invention, the degradable element 4 can be configured to degrade not only during the predetermined events. As an example, the degradable element 4 can degrade also during "normal use" of the fabric 1, e.g. when the garment comprising fabric 1 is worn by a user.

Preferably, the degradation rate (i.e. the speed of degradation) during normal use is different from degradation during the predetermined event. In particular, degradation during a preset event is greater (and preferably also faster) than degradation during normal use. In other words, the percentage of degradation during normal use is lower than the percentage of degradation during the predetermined event. Degradation is normally detected as a change in the signal generated by the sensor.

Figure 7:
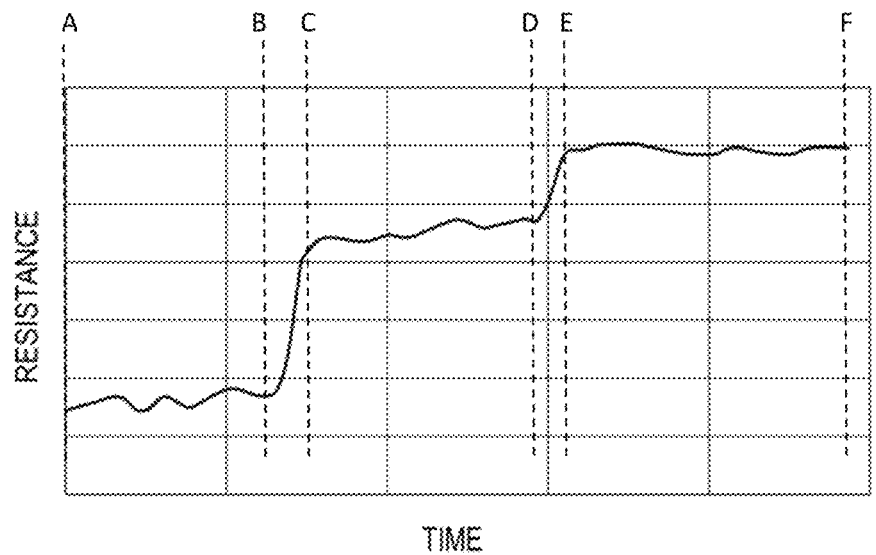
FIG. 7 is a view of the electric resistance of a water degradable resistor as a function of time, when subject to different conditions, shown schematically in FIG. 8A.
Figure 8:
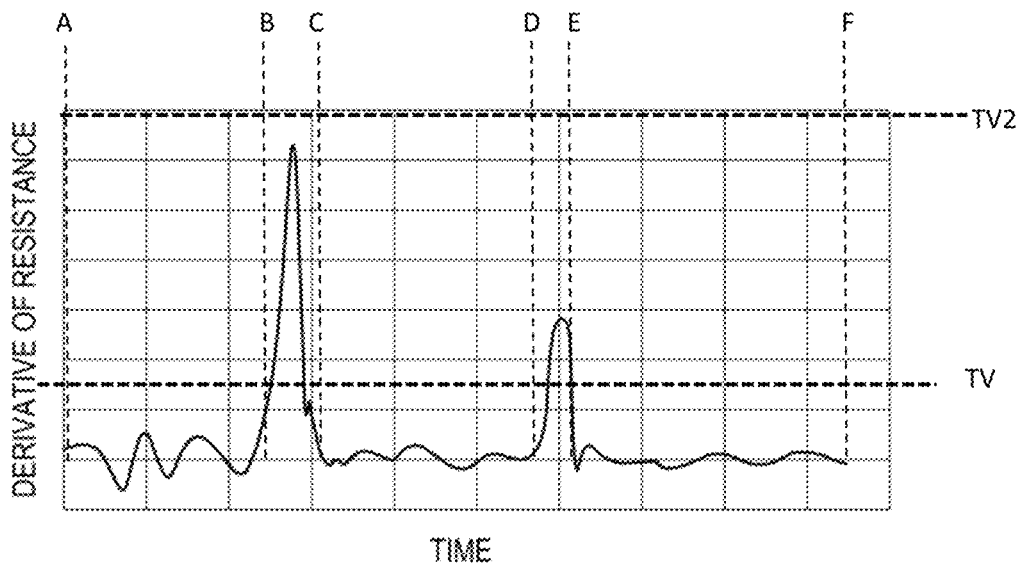
FIG. 8 is a view of the derivative of the resistance of FIG. 7 as a function of time.
Figure 8A:
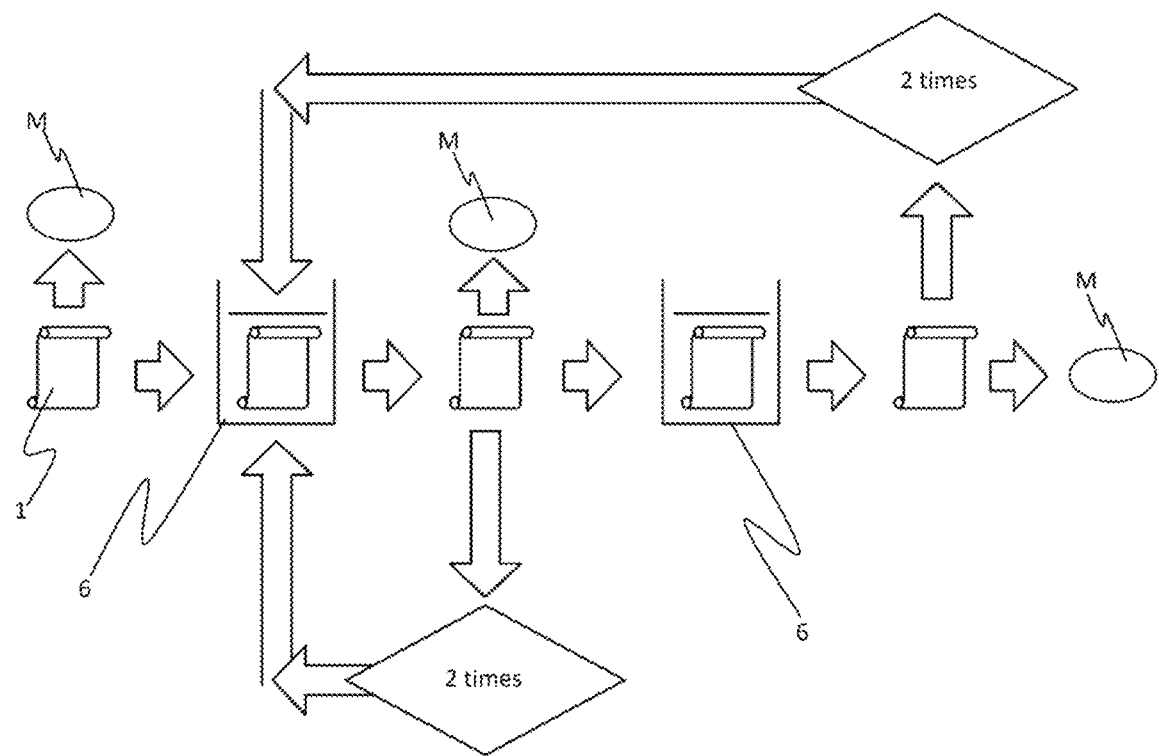
FIG. 8A is a schematic view of the different conditions of a test on a water degradable elements.

An example of such an embodiment is shown in FIGS. 7 and 8A. In particular, in FIG. 7 the result of a test carried out on a fabric 1 provided with water degradable resistor 4a is shown, to evaluate the response of the water degradable resistor during different conditions (i.e. during "normal use" and during a washing cycle). The test is shown schematically in FIG. 8A.

In particular, sweat simulations 6 (i.e. simulations of a "normal use") and washing cycles simulations 8 were carried out on a fabric 1. Sweat simulation were carried out by immersion of the fabric into a pH 5.5 solution prepared with histidine monohydrochloride monohydrate, sodium phosphate and sodium chloride.

Phases M of measuring the resistance of the water degradable resistor 4a were carried out before and after the sweat simulations 6 and the washing cycles simulations 8. As shown, two cycles of sweat simulations 6 and washing cycles simulations were carried out. After that, the fabric was placed at rest, i.e. it was not worn by a used nor subjected to particular treatment.

In more detail, with reference also to FIG. 7, between times A and B, and between times C and D, a sweat simulation 6 was performed. Between times B and C, and between times D and E, a washing simulation 8 was performed. Between times E and F, the fabric was placed at rest.

As mentioned, the result of the test of FIG. 8A is shown in FIG. 7. In particular, between times A and B, and between times C and D, a slow and little increase of the resistance of a water degradable resistor 4a (corresponding to a slow degradation of the water degradable resistor 4a) is shown. This slow degradation is due to a "normal use" of the fabric 1, e.g. to contact with the skin and sweat of a user.

Between times B and C and D and E, a fast degradation is shown. This fast degradation is due to washing cycles. In particular, it can be noted that washing cycle between time B and time C was longer than washing cycle between time D and time E. After time E, the resistance of the water degradable water resistor 4a is substantially constant. This is due to non-use of the fabric.

The behavior is not limited only to a water degradable resistor 4a. As an example, the water degradable capacitor 4b and inductor 4c can be configured to show similar behavior, e.g. a first degree of degradation during normal use, and a second degree of degradation during a heat treatment.

Piezoelectric degradable element 4d can also show a similar behavior. As an example, the heat emitted by a user body can cause a slow degradation of the polarization of the piezoelectric degradable element 4d.

Furthermore, in other embodiments, the degradable element can have a third degree of degradation, other than the degradation during normal use and the degradation during a heat treatment/washing cycle. In particular, the third degree of degradation is preferably configured to show the occurrence of an undesired event.

The third degree of degradation is typically different from the degree of degradation during the preset condition. In other words, the percentage of degradation during an undesired event is different (typically greater and/or faster) than the percentage of degradation during the preset condition.

As an example, a piezoelectric degradable element can lose a great amount of polarization if the fabric 1 is heated at a too high temperature. In an embodiment, the piezoelectric element undergoes a glass transition at a certain temperature (which is a temperature that should not be applied to the fabric 1), so as to totally lose polarization. In other words, a degradable element can be totally degraded during a single undesired event.

With reference to the embodiments previously disclosed, a water degradable element can be highly degraded (e.g. greatly eroded or dissolved) if the fabric is placed in water for a too long period.

In general, embodiments of the present invention can have a degradable element with only one degree of degradation, i.e. degradation at a preset event. Different embodiments can have a degradable element with two degrees of degradation (i.e. degradation at a predetermined event and degradation during normal use or during an undesired event).

Further embodiments can have a degradable element with all the three degrees of degradation previously discussed.

Embodiments with one degradable element 4 have been shown. It is however possible to have a greater number of degradable elements 4. Furthermore, degradable elements of different kinds can be used in the same embodiment, to monitor different events. As an example, a water degradable element can be used to count washing cycles, while a piezoelectric degradable element can be used to monitor heat treatments.

With particular reference to FIGS. 7 and 8, testing of a degradable element 4 (with particular reference to a water degradable resistor 4a) will be now discussed. The controller 10 checks an electric feature of the electric circuit 3. In the present embodiment, the controller 10 checks the resistance of the electric circuit 3. This check can be continuous, or it can be carried out at discrete time intervals, e.g. with a number of consecutive measurements each time. The variation of the monitored electric feature can show the occurrence of a predetermined event.

As before mentioned, an ADC 5 (FIG. 11) preferably transforms the monitored data into a digital signal, that can be handled by the controller 10. The variation of the monitored data are then stored in a memory of the controller 10. Thanks to this, it is possible to have the value of the monitored data as a function of time. Time information can be provided by the controller 10 itself, which can be provided with an internal clock. In the embodiment of FIG. 7, the trend of the values of the resistance of the circuit 3 over time is shown.

The variation of the monitored data (i.e. the electric feature of the electric circuit 3) is then used to evaluate the number of occurrences of a predetermined event.

Various analytic methods can be used for the purpose, e.g. real-time and on-line fast data analysis on the controller, or off-line data mining carried out e.g. by means of a PC.

In the shown embodiment, with particular reference to FIG. 8, the derivative of the function between the electric feature (the resistance in this case) and time is calculated. As known, the derivative of a function shows the degree of variation of a function. Thus, the peaks p1 and p2 of the derivative function correspond to the moments of greater variation of the monitored data. As known this great variation occurs at a predetermined event.

A threshold value can be established to evaluate the number of significant peaks p1 and p2. In other words, every time that the derivative function exceeds the threshold value, the controller counts one peak, i.e. it counts the occurrences of a predetermined event.

In the shown embodiment, two washing cycles have been carried out, i.e. between times B and C, and D and E of FIG. 7. As a result, the derivative function of FIG. 8 shows two peaks p1 (between time B and time C) and p2 (between time D and time E). These peaks are greater than the predetermined threshold value TV, and so the controller counts two predetermined events.

A further threshold value TV2, greater than threshold value TV, can be chosen in order to count the occurrences of undesired events. Thanks to this, if a peak p1 is between TV and TV2, the controller 10 will count an occurrence of a predetermined event. On the contrary if a peak is above both TV and TV2, an occurrence of an undesired event will be counted. In the shown embodiment, no undesired events were carried out on the fabric 1. As a result no peaks of the derivative function above TV2 are present.

Other methods can be used to evaluate the number of occurrences of predetermined events. As an example, tests can be carried out on different sensors 12, to evaluate the change in the relevant electrical feature at the occurrence of one or more events (e.g. washing cycles) or in the whole life-cycle of the sensors 12.

FIGS. 13A-13D show the results of a further test. Sensors on two fabric samples were tested for 2500 minutes. A first sensors was placed on a sample that did not undergo any washing (test results of FIGS. 11C and 11 D). The second sample underwent a series of washing at 60° C. The sensor of both samples was a resistor sensor.

Figure 13A:
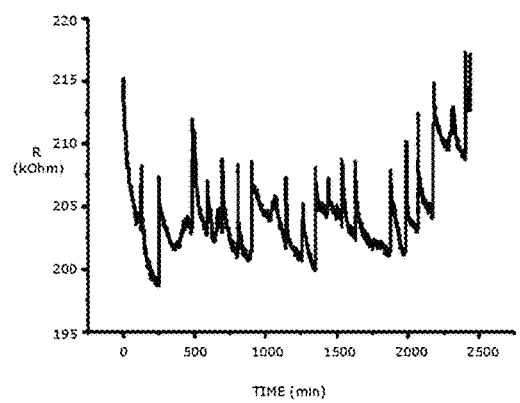
FIGS. 13A-13B show the results of a test carried out on a sensor placed on a fabric that was not subject to washing cycles.
Figure 13C:
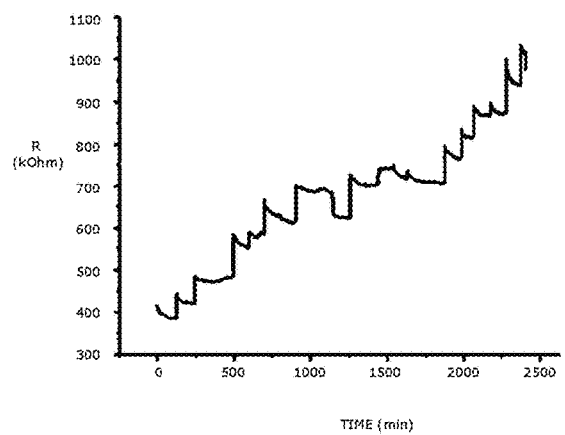
FIGS. 13C-13D show the results of a test carried out on a sensor placed on a fabric that was subject to washing cycles at 60 degrees Celsius.
Figure 13B:
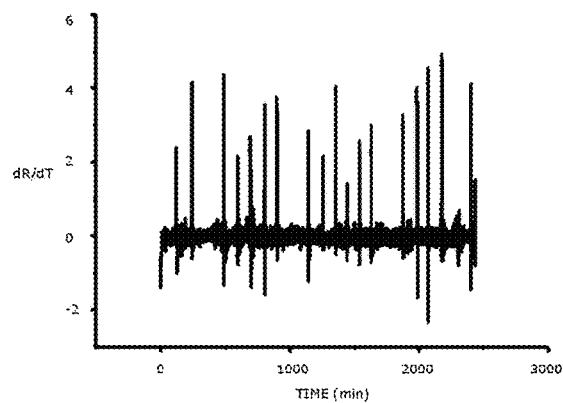

FIG. 13A shows that the resistance of the sensor on the sample that wasn't washed showed a slight fluctuation of the value of the resistance. In particular the value of the resistance ranged between 200 and 215 kΩ. Such a fluctuation is due to the response to the humidity of the environment. The derivative value (whose trend is shown in FIG. 13B) shows a number of peaks that are very low, and that are not recognized as washing events by the controller 10.

Figure 13D:
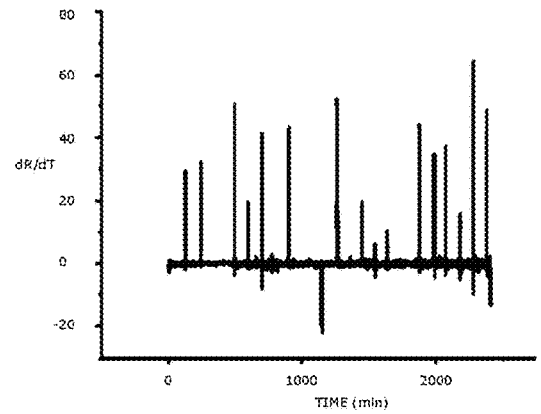

On the contrary, the sensor of the sample that was subjected to washings changed sensibly its resistance value, in fact a total variation of over 600 kΩ is shown in FIG. 13O. Each washing cycle caused the reduction in the degradable portion of the sensor, so as to rapidly (and sensibly) increase the value of the relevant resistance. As a result, the derivative value of FIG. 13D shows higher peaks with respect to the one of FIG. 13B (please note that the ratio of the scale on the y-axis is 1:10). As per before, these peaks are thus identified by the controller 10 as washing cycles.

Figure 12:
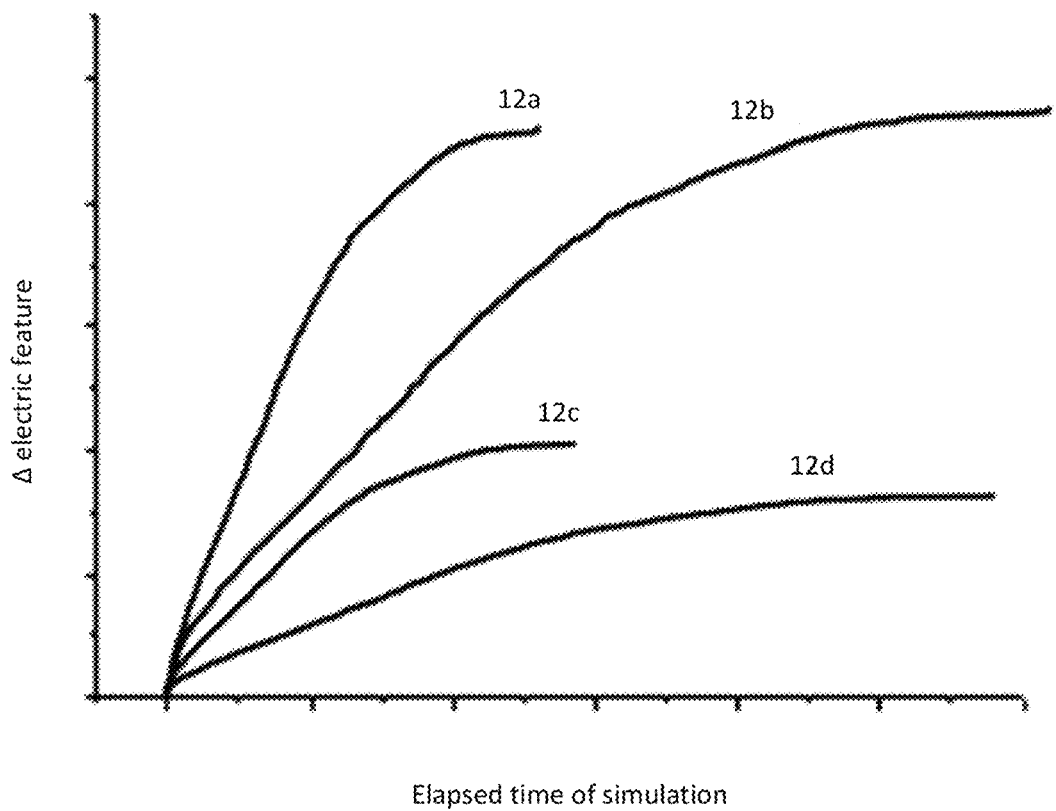
FIG. 12 is a view of the variation of the electric feature of different degradable elements.

FIG. 12 shows the result of a simulation of the life-cycle of four different sensors 12, identified by references 12a, 12b, 12c and 12d.

The sensors 12a, 12b, 12c and 12d where put in a strong chemical bath, to simulate the whole life of the sensors 12a, 12b, 12c and 12d.

As can be seen, sensor 12a is a provided with a particularly high "sensitivity" to the event (i.e. it provides a sensibly great and fast variation of the electric feature), but it is provided with lower lifetime with respect to the other sensors 12b and 12d. In fact it can be seen that the curve of sensor 12a in FIG. 4 becomes substantially flat earlier than the other sensors 12b and 12d. Sensor 12c provides a behavior similar to sensor 12a but with lower sensitivity to the event (sensor 12c would thus cause smaller steps in a graph as the one of FIG. 7 or lower peaks in a graph as the one of FIG. 8). Sensors 12b and 12d are provided with a much longer lifetime than sensor 12a and 12c, wherein sensor 12b has greater sensitivity than sensor 12d (resembling the relationship between sensors 12a and 12c respectively).

In general, from the results of these or similar tests, it is possible to configure the controller 10 to evaluate the response of each of the sensor 12a, 12b, 12c and 12d, e.g. to predict the variation of the electric feature (i.e. the height of the steps of FIG. 7), to predict the speed of variation of the electric feature (i.e. the pendency of the steps of FIG. 7 and thus the height of the peaks of FIG. 8).

Furthermore, from these results, it is possible to predict the end of life of the sensors 12a, 12b, 12c and 12d, that is when there is substantially no variation in the electric feature of the sensor 12a, 12b, 12c and 12d in response to an event (washing cycle), i.e. when, at their end, the curves of FIG. 12 become substantially flat.

In general, the controller 10 can be configured to recognize the variation of the value of the electric feature in response to certain events, e.g. a washing cycle. Further analytic methods can be carried out to evaluate the "normal use" carried out on the fabric. As an example, a small variation of the resistance that happens in a long time, e.g. the small variation between times C and D of FIG. 7, can be recognized by the controller 10 as "normal use". In general, the controller 10 can be provided with algorithms to associate the amplitude of each jump to a certain event.

In general, the evaluation of the monitored data (e.g. the resistance of FIG. 7) allows the controller 10 to estimate the life-cycle of a fabric 1 (and thus of garments having fabric 1), i.e. the events carried out on the fabric 1. In particular, the evaluation of the monitored data can be used to estimate the events carried out on the fabric 1, and possibly to monitor and distinguish between each other different kinds of events (e.g. washing cycle and/or heat treatments and/or normal use and/or undesired events, etc.), occurred on the fabric 1.

The invention claimed is:

1. A fabric comprising at least one conductive element defining at least a portion of an electric circuit, and a sensor coupled to said conductive element, wherein the sensor comprises a degradable element configured to provide a plurality of degrees of degradation of the degradable element itself in preset conditions to change an electric feature of said sensor.

2. The fabric according to claim 1, wherein the fabric is a woven or knitted fabric.

3. The fabric according to claim 1, wherein the conductive element comprises conductive yarn.

4. The fabric according to claim 1, wherein said preset conditions comprise at least one of a cleaning cycle, a heat treatment and wearing conditions.

5. The fabric according to claim 1, wherein said degradable element is configured to reduce its mass or dimension when put in contact with a liquid, to vary said electric feature.

6. The fabric according to claim 5, wherein the change of said electric feature of said sensor upon said degradation in said preset condition comprises a change between 1% and 5%.

7. The fabric according to claim 1, wherein said degradable element comprises at least one of a resistor and a dielectric portion of a capacitor interposed between two conductive elements.

8. The fabric according to claim 1, wherein said degradable element comprises a core of an inductor that defines the inductance of said inductor or includes a conductive element wound around said degradable element.

9. The fabric according to claim 1, wherein said degradable element comprises a piezoelectric element.

10. The fabric according to claim 9, wherein the change of the electric feature upon said degradation comprises a change of 10% to 50%.

11. The fabric according to claim 4, wherein the degradable element is configured to provide a first degree of degradation when the fabric is worn by a user, and a second degree of degradation at said cleaning cycle or at said heat treatment.

12. The fabric according to claim 11, wherein the degradable element is further configured to provide a third degree of degradation due to an undesired event being different from said preset condition.

13. An article comprising a fabric according to claim 1.

14. The article according to claim 13, further comprising a controller coupled to said sensor to monitor the change of said electric feature.

15. The article according to claim 14, wherein said controller is disposed within a button of said article.

16. The article according to claim 13, wherein said article is a garment.

17. The article according to claim 16, wherein the garment comprises at least one seam, and the sensor is disposed within said at least one seams.

18. The article according to claim 17, wherein said garment is a pair of pants and said controller is disposed within a button of said garment.

19. The article according to claim 18, wherein said sensor is disposed within at least one of an outer lateral seam extending in a longitudinal direction along a wearer's leg and an inner medial seam extending in said longitudinal direction along said wearer's leg.

20. A process for monitoring life-cycle of a fabric, said process comprising:
   (a) providing a fabric with at least one conductive element defining at least one portion of an electric circuit, and a sensor coupled to said conductive element, said sensor having a degradable element configured to at least partially degrade in preset conditions, whereby degradation of said element changes an electric feature of said sensor;
   (b) monitoring said electric feature and storing said monitored electric feature;

(c) evaluating at least one of a value of said degradation of said electric feature and a number of degradation events as a function of said monitored and stored data;

(d) determining status of said fabric as a function of the evaluation.

21. The process according to claim 20, wherein said step (c) comprises the steps of:
- (c1) evaluating a function of the monitored electric feature as a function of time;
- (c2) evaluating a derivative of the function of the monitored electric feature of step (c1)
- (c3) counting peaks of the derivative function, wherein each said peak is associated with one occurrence of said degradation event.

22. The process according to claim 20, wherein said sensor comprises at least one of resistor, an inductor, a capacitor and a piezoelectric element.

23. An electric circuit comprising at least one conductive element defining at least one portion of said electric circuit and a sensor coupled to said conductive element, the sensor including a degradable element configured to provide a plurality of degrees of degradation of the degradable element itself in preset conditions to change an electric feature of said sensor, said circuit being suitable to be inserted into a fabric.

24. A fabric comprising at least one conductive element to define at least one portion of an electric circuit, and a sensor coupled to said conductive element, wherein the sensor comprises a degradable element configured to provide a plurality of degrees of degradation in preset conditions to change an electric feature of said sensor, wherein said preset conditions comprise at least one of a cleaning cycle, a heat treatment and wearing conditions and wherein the degradable element is configured to provide a first degree of degradation when the fabric is worn by a user, and a second degree of degradation at said cleaning cycle or heat treatment.

25. The fabric according to claim 24, wherein the degradable element is provided with a third degree of degradation at an undesired event, different from said preset condition.

* * * * *